United States Patent [19]
Perlman

[11] Patent Number: 5,858,770
[45] Date of Patent: Jan. 12, 1999

[54] CELL CULTURE PLATE WITH OXYGEN AND CARBON DIOXIDE-PERMEABLE WATERPROOF SEALING MEMBRANE

[75] Inventor: Daniel Perlman, Arlington, Mass.

[73] Assignee: Brandeis University, Waltham, Mass.

[21] Appl. No.: 940,422

[22] Filed: Sep. 30, 1997

[51] Int. Cl.$^6$ .................................................. C12M 3/00
[52] U.S. Cl. .................................. 435/305.3; 435/305.4; 435/297.5
[58] Field of Search .................................. 435/325, 374, 435/243, 260, 297.1, 297.5, 305.1, 305.3, 305.4, 307.1; 422/102

[56] References Cited

U.S. PATENT DOCUMENTS

| | | | |
|---|---|---|---|
| 3,946,780 | 3/1976 | Sellers | 435/297.1 |
| 5,486,475 | 1/1996 | Kramer et al. | 435/266 |

FOREIGN PATENT DOCUMENTS

| | | | |
|---|---|---|---|
| 2 269 391 | 9/1994 | United Kingdom | 435/305.3 |

OTHER PUBLICATIONS

*Nunc™ Products 1996 catalog*, Nalge Nunc International, pp. 3, 8, 23 (1996).

Sealplate™ Product Description, *PGC Scientifics 1995–1996 General Catalog of Laboratory Equipment and Supplies*, pp. 77 (1995–1996).

*3M™ Tegaderm™ and 3M™ Tegaderm™ HP Transparent Dressings Product Profile*, 3M Health Care, St. Paul, MN (1995).

S/C Urethane Film, Product #8167–08 Product Description, *MEDCO Coated Products Prodcut Data Sheet*.

*An Evaluation of Bioclusive™ Transparent Dressing for Cleaning Surgical Wounds: Interim Analysis*, Johnson & Johnson Medical, Inc., Oct. 5, 1985.

Firm Rubber–Faced Lightweight Brayer, Model #24 Product Description, *Testrite Information Sheet*, Testrite Instrument Company, Newark, NJ (1995).

*Primary Examiner*—David A. Redding
*Attorney, Agent, or Firm*—Lyon & Lyon LLP

[57] ABSTRACT

A cell culture plate which contains cells incubated in a liquid medium held in sample wells formed and arranged over the surface of the plate, is covered and sealed with a waterproof adhesive sealing membrane which excludes microbial contaminants, but which is functionally permeable to oxygen and carbon dioxide gases. The membrane allows cellular respiration to continue, with the transmission rate of oxygen and carbon dioxide through the membrane being essentially uniform from well to well over the surface of the plate.

11 Claims, 1 Drawing Sheet

100% CELL CULTURE PLATE WITH OXYGEN AND CARBON DIOXIDE-PERMEABLE WATERPROOF SEALING MEMBRANE

BACKGROUND OF THE INVENTION

This invention relates to a cover for a multi-sample container, of a variety known as a "cell culture plate" or a "microtiter plate" for culturing and manipulating living cells. Specifically, the invention concerns cell culture plates in which the plate is sealed with an oxygen and carbon dioxide-permeable waterproof sealing membrane.

Cell culture plates including the so-called "multiwell microliter plates" (herein collectively abbreviated and termed "culture plates" or "plates") are shallow plastic vessels with multiple compartments, i.e., sample wells, which are used for holding growth medium for culturing cells. Culture plates are currently manufactured from polystyrene, polyethylene, polypropylene, polycarbonate, and polyvinyl thermoplastic resins using conventional injection-molding or thermoforming methods. The most common present day culture plates measure approximately 3 inches by 5 inches and are physically described, depicted and commercially available in most scientific supply catalogs (see, for example, Nunc Products 1996 catalog, Nalge Nunc International, Naperville Ill.). Culture plates typically contain between 4 and 384 sample wells per plate. Depending upon the size of wells in a plate, the liquid capacity of each well ranges from approximately 100 microliters to 2 milliliters.

Living cells contained in the sample wells of culture plates can be tested or assayed for physical, chemical and biological properties during or after cell growth using biochemical and immunochemical techniques and reagents. Growth and/or reliable testing of cells in the multiple wells of such plates depends upon the plates being free of cytotoxic substances, ongoing sterility being maintained within the wells of the plates, and uniform dependable oxygen and carbon dioxide exchange into and out of the wells. For maintaining sterility, either of two commercially available covers may be used on the plates during or after cell growth. The covers protect not only living cells within the sample wells, but also their metabolites and any associated sterile reagents added to the wells. The first type of cover is principally used during cell growth, and is a loose-fitting molded plastic lid which overhangs the plate to exclude particulate contaminants (such as bacterial contaminants), while allowing exchange of gases for support of cellular respiration and cell growth. The second type of cover is an essentially gas-impermeable adhesive polyester, polypropylene, or polyethylene plastic sealing film (e.g., Sealplate™, manufactured by Excel Scientific, Inc., Wrightwood, Calif.). Such sealing films function to seal each sample well, and prevent well to well contamination and sample evaporation, while being chemically inert so as to allow chemical processing steps to be carried out in the plate. Since this second type of cover is gas-impermeable, it is only applied to the plate following cell growth. It is most useful for freezer storage, preservation, and the chemical processing of cells and other micro-samples.

SUMMARY OF THE INVENTION

In general, the present invention is directed toward improving the multiwell cell culture plate, by providing a gas-permeable, leak-proof, and adhesive membrane for sealing such plates. Culture plates generally have a multiplicity of compartments, i.e., four or more sample wells, which are used for holding and culturing living cells. Because an adhesive covering and sealing membrane has been found which is oxygen and carbon dioxide-permeable, i.e. "breathable", as well as being waterproof and non-cytotoxic, living cells of either eukaryotic or procaryotic origin, can grow and thrive within a sealed leak-proof culture plate. A variety of cell types including mammalian and bacterial cells have been shown to retain normal viability and growth rates after they and their culture medium contact the membrane. An example of a useful membrane is one that is generally thin and composed principally of polyurethane polymers, e.g., one that is currently used as a moisture-permeable surgical dressing. It does not peel off any of culture plates tested, nor allow any aqueous liquids to leak through either when inverted with liquid culture medium held in the sample wells, or when placed in an incubator at 37° C. and 100% relative humidity. The addition of an oxygen and carbon dioxide-permeable sealing membrane provides benefits and allows cell manipulation procedures in a culture plate to be routinely carried out, which were not previously practical. Procedures which previously required chemical assay steps with living cells, required the use, (albeit brief so as not to kill the cells) of gas-impermeable sealing membranes (sealed to permit liquid shaking, inversion of the plate, etc.). Such procedures can now be carried out easily and over longer time intervals because breathable sealing membranes allow respiration, cell viability and cell growth to be maintained in the shaken and inverted leak-proof culture plates. In fact, many cellular-based assays depend upon continuing respiration for accuracy and reproducibility of the assays, and an extended period of ongoing cellular metabolism may be required for cells held in such plates. Furthermore, Applicant has discovered that while prior art hard plastic covers allow rapid gas exchange around their perimeters, they allow a diminishing rate of gas exchange toward the center of the plate. This limitation is overcome by the membranes of the present invention which assures uniformity of gas exchange and thus cellular respiration from well to well and sample to sample across the entire plate. This uniformity is important for experimental accuracy and valid comparisons among different cell samples held in different wells within a plate.

Considering the prior covers more specifically (see above), cover type (i) is impermeable and fabricated of rigid plastic which, as a loose-fitting cover, allows gas exchange (via leakage and exchange of oxygen and carbon dioxide around the perimeter of the plate) and cell growth. On the other hand for cover type (ii), the prior cover includes sterile impermeable adhesive sealing films which create a waterproof and microbe-impermeable seal over and around each well. Significant limitations exist in the use of both of these two covers. In fact, there are many analytical procedures which cannot be carried out efficiently in culture plates due to limitations in the utility of these covers identified by Applicant. More specifically, the use of a plastic cover, (i), which allows general cell growth to continue, is not ideal because Applicant has discovered that gas exchange is non-uniform from sample well to sample well across the culture plate. Wells adjacent the corners and edges of the plate experience a higher rate of gas exchange than the more distant wells nearer the center of the plate. Consequently, cellular-based assays which depend upon uniform cellular respiration and oxygen tension among the sample wells, may suffer from variable or unreproducible results from well to well across the plate. On the other hand, the use of the prior art sealing film, (ii), provides only a waterproof barrier useful for storing and freezing cells, and useful for chemical, biochemical and immunological assay of cells. For example, chemical and biochemical reagents can be placed into sample wells containing cells, and the sealing film allows the reagents in the culture plate to be shaken without leakage or well to well cross-contamination. However, such a sealing film does not allow cellular respiration to continue. Therefore, the sealing film does not allow a prolonged or continuous incubation of living (respiring) cells with reagents. In fact, the combined or sequential use of the covers (i) and (ii) does not in any practical sense allow continuous incubation of living cells in a culture plate, with simultaneous inversion and/or shaking, for example, to maintain a mixed suspension of living cells and reagents.

Applicant has discovered that in the technology area of human wound care dressings, the sterile moisture-permeable, flexible membranes which have become commercially available for application to the skin (following surgery, wound injury or burn injury) are also highly permeable to oxygen and carbon dioxide. These membranes are typically thin (approximately 1 mil, i.e., 0.001 inch thick) and fabricated from a moisture-permeable copolymer such as polyester-polyurethane or polyether-polyurethane. Moisture permeation through the membrane is important for its wound care use, so that the membrane does not trap liquid perspiration (from sweat glands in the skin). While these wound dressing membranes are thin, they do not allow either microorganisms or viruses to pass through. Consequently, when applied and adhered to a culture plate as described in the present invention, microbial contaminants are likewise excluded from the sample wells of the plate. Those in the art will recognize that any adhesive and non-cytotoxic membrane that is impermeable to microorganisms such as bacteria, mycoplasma and even viruses is useful in this invention so long as sufficient oxygen and carbon dioxide-permeability exists through the membrane. The amount of gas permeability necessary will depend on the experiment to be conducted, but will generally be comparable to the membranes exemplified herein. Standard tests can be used to determine adequate permeability for the purposes of this invention, as well as the other preferred features of the membranes noted below.

DEFINITIONS

For the purposes of this invention, and to aid in the selection of appropriate scaling membrane materials and related component materials for covering and sealing culture plates, it is important to define a number of technical and generally descriptive terms used in the text, and in the claims. The term "a waterproof adhesive sealing membrane" refers to a thin sheet material, i.e., a manufactured film, which blocks any measurable permeation by liquid water and aqueous solutions, and which is coated on its lower surface with a pressure-sensitive adhesive. Furthermore, neither the film nor the adhesive can dissolve in water, nor leach any measurable quantity of substances harmful to the growth of cultured eukaryotic and prokaryotic cells during exposure to aqueous solutions, nutrient growth medium, and the like. In the context of the properties of the membrane, the term "excludes microbial contaminants: refers to the ability of the membrane when attached to a cell culture plate, to prevent penetration of bacteria and viruses which are placed on the outside, i.e., upper surface of the membrane. The membranes described in the present invention, and previously used a wound care dressings, have been thoroughly tested for their ability to exclude a wide range of bacteria and viruses. The term "permeable" in the context of membrane permeability to oxygen and carbon dioxide is defined in the "Example" presented below. The term "cellular respiration" refers to the metabolic processes in a living cell which are dependent upon availability of oxygen to the cell, to generate energy for cellular growth and other functions, and the removal and balancing of carbon dioxide in the immediate environment of the cell for maintaining normal pH within the cell. The term "sufficiently permeable" in the context of oxygen and carbon dioxide permeability of a membrane, is a relative term referring to the functional ability of a membrane to allow essentially the same rate of cell growth and rate of pH equilibration (in the liquid medium surrounding cells in the sample wells of the culture plate), upon comparison with identical cells grown in a culture plate covered with a conventional loose-fitting hard plastic cover. The term "essentially uniform transmission rate" refers to the absence of variability in the rate of membrane permeation by oxygen and carbon dioxide as observed across the length and width of a given membrane covering a cell culture dish (see "Example" presented below). It is also useful to define several liquid media used for incubating, washing and treating cells. Thus, "nutrient growth medium" is a liquid which is used to feed living cells and support their growth, and contains vitamins, essential nutrients, salts and the like. "Incubation buffer medium" is a liquid which helps sustain cellular viability and electrolyte balance in a cell, without containing the nutrients to support cellular growth and proliferation. "Buffered enzyme medium" is equivalent to an "incubation buffer medium", bu also containing one or more enzymes which are included to alter the cells or their metabolites. Thus trypsin, the digestive enzyme, may be added to an incubation buffer medium to help disaggregate aggregated or cohered eukaryotic cells. "Chemical, biochemical or immunochemical assay medium" is equivalent to an "incubation buffer medium", but also contains one or more chemical, biochemical or immunochemical reagents which react with cells and/or metabolites produced by cells to help identify individual cells or groups of cells, and/or to help measure the level of a metabolite (e.g., a small molecule such as a sugar or amino acid, or a macromolecule metabolites such as an antibody) produced by such cell(s), or to measure and/or detect some other biochemical marker being studied in the cell(s). An immunochemical reagent can include, for example, a specific antigen used to detect the presence of an antibody or antibodies produced by a cell or group of cells, or alternatively, an antibody reagent used to complex with, and detect a desired antigen. The term "facestock material", refers to a substrate film whose lower surface, in the present invention, is coated with an adhesive. The substrate film or facestock is typically formed from an extruded or cast polymer or copolymer sheet material. Additional sheets or films may be added to the upper surface of the facestock, such as a removable carrier film, to provide additional rigidity to thin facestocks, to aid in the manual handling and aligning of the membrane on the culture plate. Furthermore, a removable release sheet may be attached to the lower surface or adhesive coating on the facestock to protect the adhesive from contaminating substances such as microbes, prior to use. The term "removable", in the context of a sheet or film is defined as manually peelable. The term "non-cytotoxic" refers to the cell compatibility of a material (such as the facestock material and pressure-sensitive adhesive used herein) which allows that material to remain in contact with living cells and the liquid medium being used to bathe and/or incubate these cells, without the metabolism, growth rate, and viability of the cells being adversely affected. The term "sterile" or "sterility" as used herein, refers to the absence of any active microbes, i.e., any viable cellular contaminants, mycoplasma, and/or infectious viruses and phages. By definition, when a sealing membrane is adhesively attached to a culture plate, and is capable of "excluding" microbial contaminants, it can "maintain the sterility" in the sample wells of the plate. That is, the pore size of the membrane is too small to allow passage of microbes. Likewise, a removable release paper (such as a conventional 50 pound Kraft release paper) is typically used to cover and protect the lower surface of the membrane and the adhesive coating material thereon, and serves to maintain the sterility of this surface and coating prior to use.

In a first aspect, the present invention features a cell culture plate containing cells which are incubated in a liquid medium contained in sample wells formed and arranged over the surface of the plate. The plate is covered and sealed with a waterproof adhesive sealing membrane which excludes microbial contaminants, but is functionally permeable (as defined above) to oxygen and carbon dioxide gases, allowing cellular respiration to continue, with the transmission rate of these gases through this sealing membrane being essentially uniform from well to well over the surface of the plate.

In preferred embodiments, the liquid medium used for incubation of the cells in these culture plates is selected from the group consisting of nutrient growth medium, incubation buffer medium, buffered enzyme medium, chemical assay medium, biochemical assay medium, and immunochemical assay medium. For example, growth media having defined compositions are well known in the art such as Eagles and Dulbeccos media for eukaryotic cells, and Luria's broth and M9minimal media for bacterial cells. Similarly, cell incubation buffers and buffered enzyme solutions of defined compositions are known, such as phosphate buffered saline (PBS) and PBS with trypsin enzyme for disaggregating and resuspending cells. Likewise, numerous buffered chemical, biochemical and immunological solutions have been defined and used in these culture plates. In other preferred embodiments, the adhesive sealing membrane includes a facestock material selected from the group consisting of polyester-polyurethane copolymer film and polyether-polyurethane copolymer film. These copolymers and thin films (such as 0.001 inch thick films) formed with these copolymers are known in the field of surgery and wound care because these films are substantially moisture-permeable. In a particularly preferred embodiment, the facestock of these films has a thickness ranging between 0.0005 and 0.002 inches. This thickness range not only allows water vapor permeation, but also allows adequate diffusion of $O_2$ and $CO_2$ to support cell respiration and growth in the culture plates.

In still another embodiment, the bottom, i.e., the lower surface, of the sealing membrane is coated with a non-cytotoxic pressure-sensitive adhesive material which adheres the sealing membrane to said culture plate. In a more preferred embodiment, the adhesive is a non-cytotoxic pressure-sensitive acrylic adhesive material.

In a second related aspect, the present invention features a kit which includes a culture plate for culturing living cells which are incubated in a liquid medium placed in sample wells formed and arranged over the surface of the culture plate, and a sterile sheet assembly which includes a sized portion of the waterproof sealing membrane described above in the first aspect of the invention.

In preferred embodiments, the sized portion of membrane includes a first lower surface which is coated with a non-cytotoxic pressure-sensitive adhesive material for attaching the membrane to the culture plate; the pressure-sensitive adhesive material is covered and protected by a removable release paper sheet which serves to maintain the sterility of the first lower surface and this pressure-sensitive adhesive material; the sterile sized portion of membrane has a second upper surface which is at least partially covered by a removable upper carrier sheet which aids in handling and aligning the thin and floppy membrane during its attachment to the culture plate; and the removable upper carrier sheet is selected from the group consisting of a peelable transparent plastic sheet, and a peelable release paper frame configured and arranged around the perimeter portion of the membrane.

In a third related aspect, the invention features a sterile sheet assembly which includes a sized portion of waterproof adhesive sealing membrane which is functionally permeable (as defined above) to oxygen and carbon dioxide gases. The membrane includes a first lower surface which is coated with a non-cytotoxic pressure-sensitive adhesive material for attaching the membrane to a culture plate. The adhesive material is protected by a removable release paper sheet which serves to maintain the sterility of this first lower surface and adhesive material. The release paper sheet is cleaved, i.e., fully scored or cut through its thickness and across its width at two locations, with each of two cleavages positioned not less than 0.2 inches, and not more than 1.5 inches from each of the two ends of the assembly. These two cleavages define the boundaries of two release paper-covered end tabs for manually handling, aligning and adhesively attaching the membrane to the culture plate after the remainder of the release paper sheet has been stripped away from the adhesive surface.

In preferred aspects, the sterile sheet assembly is provided which includes a sized portion of waterproof adhesive sealing membrane which is functionally permeable to oxygen and carbon dioxide gases. The membrane includes a first lower surface which is coated with a non-cytotoxic pressure-sensitive adhesive material for attaching the membrane to a culture plate. The adhesive material is protected by a removable release paper sheet which serves to maintain the sterility of the first lower surface and the adhesive material. The membrane includes a second upper surface which is at least partially covered by a removable upper carrier sheet which provides a degree of rigidity for manually handling the thin and floppy membrane during its alignment and attachment to the culture plate. The assembly includes at least one edge-notch along its length. This notch is cut through all of the layers of the sheet assembly, and is positioned, i.e., is notched, not less than 0.2 inches, and not more than 1.5 inches from the end of the assembly. The notch allows convenient shearing force-separation, peeling and removal of the upper carrier sheet after the membrane has been adhered to the culture plate. Removal of this upper carrier sheet is necessary before functional permeability to $O_2$ and $CO_2$ can be achieved by the membrane. In a preferred embodiment of this aspect, the edge-notch in the sheet assembly extends no more than 0.25 inches inward from the edge of this sheet assembly, and the geometric shape of this edge-notch is selected from the group consisting of a V-notch, a cove cut (U-shaped notch), and a straight slit.

Other features and advantages of the invention will be apparent from the following description of the preferred embodiments, and from the claims.

DESCRIPTION OF THE PREFERRED EMBODIMENTS

APPARATUS

Figure 1:
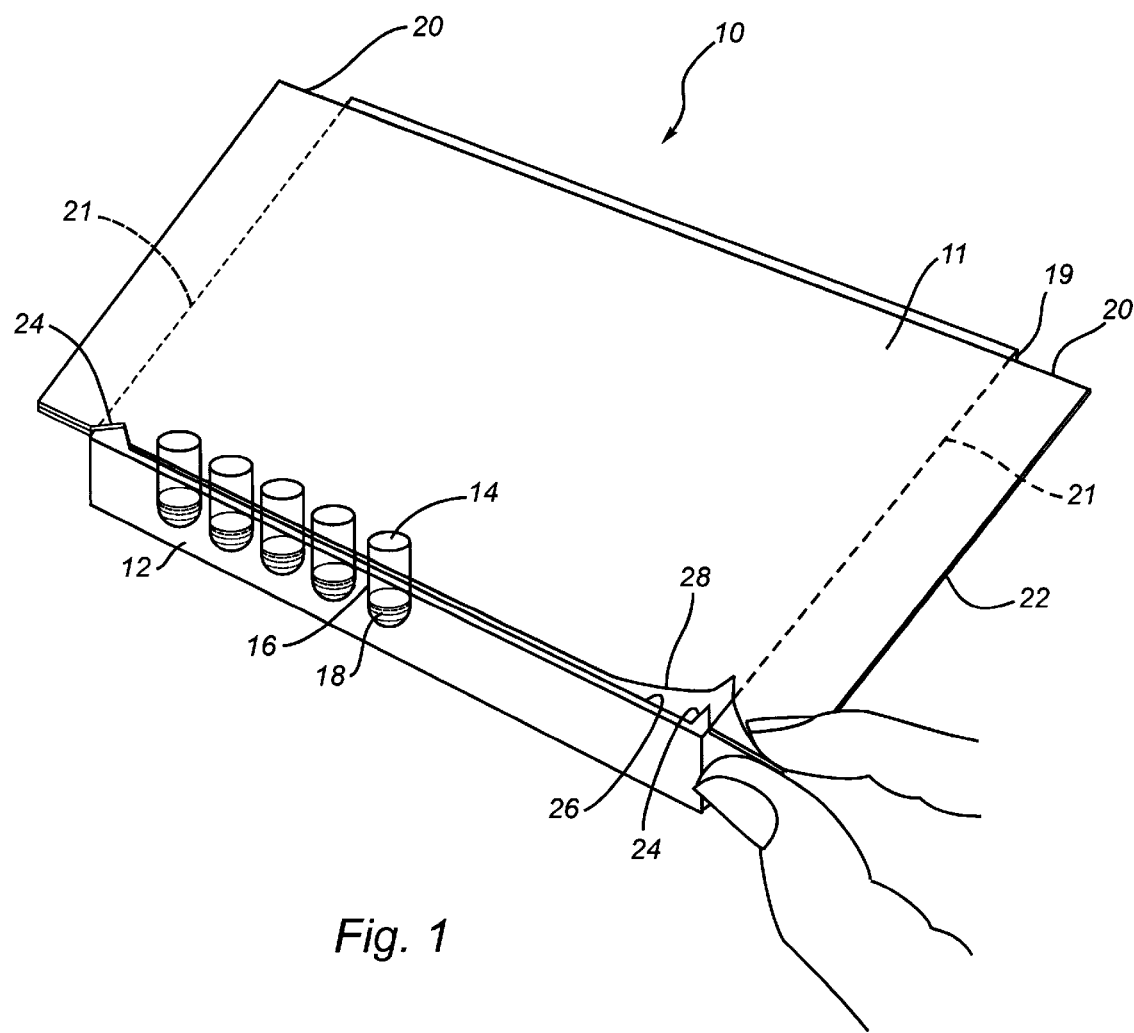
FIG. 1 is a perspective view in partial section showing a gas-permeable membrane attached to a cell culture plate, and an upper carrier sheet being separated for removal from this membrane.

Referring to FIG. 1, covered cell culture plate 10 is assembled from a sterile sheet assembly 11 and a cell culture plate 12. Sheet assembly 11 consists of three layers, an upper layer which serves as a carrier sheet 28, a middle layer which functions as the breathable adhesive sealing membrane 26, and a lower layer which functions as a release paper sheet 22 to protect the adhesive coating. The culture plate 12 contains a rectangular matrix of sample wells, e.g., ninety-six wells, 16 (only five of which are shown) whose 0.25 inch diameter openings 14 lie on the surface, or just above the surface of plate 12. These wells 16 typically contain buffered liquid 18, e.g., cell growth medium and living cells which require free exchange of oxygen and carbon dioxide gases for respiration. Sheet assembly 11 is elongated with end portions 20 which overhang the end 19 of the cell culture plate to facilitate manual handling and aligning the sheet assembly on the culture plate 12. Before adhering sheet assembly 11 to culture plate 12, a release paper sheet 22 is peeled from the underside of assembly 11 except on end portions 20 of the assembly where parallel cleavages, i.e., scoring cuts 21 across the underside of assembly 11, and through release paper sheet 22 allow the paper to remain adhered to the underside of end portions 20. The sterile adhesive underside of sheet assembly 11 is aligned and uniformly adhered to the top of culture plate 12 using a clean and compliant rubber faced ink brayer to establish uniform surface adhesion. Next, one of the corners of the end portion 20 of sheet assembly 11 is pulled gently to the side using ones fingers as shown. During this pulling, notch 24 (previously cut through all of the layers of the sheet assembly 11) serves to focus sheering forces between the two remaining layers (membrane 26 and carrier sheet 28) of sheet assembly 11, allowing a physical separation, peeling, and removal of upper carrier sheet 28 (transparent polyethylene which is not very stretchable) from a breathable waterproof adhesive sealing membrane 26 (polyether or polyester-polyurethane which is very stretchable) which remains on the cell culture plate.

EXAMPLE

While the moisture permeability of a membrane may be important for a wound dressing, Applicant was concerned with the oxygen ($O_2$) and carbon dioxide ($CO_2$) exchange rates across a given membrane, because these rates must be adequate to sustain normal respiration of living cells held in culture plates. Accordingly, a two part test method was developed which can be used to determine whether a particular membrane is suitable and useful for the purposes of the present invention. As described below, $CO_2$ permeability was monitored by rate of color change of a pH indicator in the nutrient growth medium in culture plate, while $O_2$ permeability and lack of cytotoxicity were coordinately monitored by cell growth rate (versus identical "control" cells grown in a culture plate with a conventional hard plastic cover). Two wound dressings were initially tested, one a 1 mil thick polyether polyurethane membrane known as Tegaderm™ manufactured by 3M Health Care, St. Paul, Minn., and the other, a similar 1 mil thick polyurethane membrane known as S/C urethane film product #8167-08 manufactured by Medco Coated Products, Bedford, Ohio. The ability of these membranes to allow exchange of $CO_2$ was monitored in a cell culture "gas incubator" in which 5% $CO_2$-95% air is fed to the cells. Three identical culture plates (with 96 wells), all containing Eagles cell growth medium (with phenol red pH-indicator for monitoring incoming dissolved carbon dioxide) were used in this experiment. One plate was covered with a standard commercial rigid plastic lid, while the other two were adhesively "sealed" with the breathable membranes of the present invention. When placed in a gas incubator, as carbon dioxide diffuses into growth medium held in a standard culture plate covered with a conventional plastic lid (i), the color of the pH indicator changes from dark pink to reddish-orange as the pH increases. Observations were made on the pH indicator color change in individual sample wells, comparing the conventionally covered plate with the membrane-sealed plates, as a function of time in the incubator. Observations showed that $CO_2$ exchange occurred in all plates. However, $CO_2$ transfer (color change) was slowest in the center area of the conventionally covered plate. Color change was more rapid in the perimeter area of this conventionally covered plate, and comparable to rate of color change in the membrane-sealed plates.

For the purposes of the present invention, the approximate equality or parity between the $CO_2$ transfer rate (measured by observed rate of pH indicator color change) in conventional lid-covered culture plates, and the two breathable membrane-covered plates defines the breathable membranes used in the present invention as functionally $CO_2$-permeable. Similarly, comparable cell growth rates observed for hybridoma cells cultured under the conventional lid and the two membrane coverings, defined the breathable membranes as being functionally $O_2$-permeable.

Of significant benefit and utility is the elimination of well to well experimental variability due to variable gas exchange rates with cellular-based assays. The polyurethane membrane-sealed plates showed complete uniformly of indicator color change from well to well across the plates. Moreover, the waterproof acrylic adhesives present on both the 3M and Medco polyurethane membranes, and used to adhere them to the culture plates were shown to be non-cytotoxic. This conclusion was based upon culturing varying dilutions of mouse-human hybridoma cells initially suspended in growth medium on the adhesive underside of the membranes (inverting the culture plates, with the adhesive surface facing downward). All cell dilutions grew up to normal confluent cell densities indicating that the membranes and adhesives have no detectable degree of cytotoxicity.

Besides providing uniformity of gas exchange across the culture plates, the breathable adhesive sealing membranes of the present invention allow new, simplified, and more rapid cellular-based assays and procedures to be carried out in culture plates using these membranes. In addition to the two membrane materials described and tested above, a number of other membrane films typically used as moisture-permeable surgical and skin-protective dressings are commercially available and can function as $O_2$ and $CO_2$-breathable membranes which also exclude microorganisms and viruses, including the transparent Bioclusive™ membrane manufactured by Johnson and Johnson Medical, Inc. (Arlington, Tex.).

To minimize the chance of liquid leakage around sample wells across the culture plate, it has been found that following manual alignment and initial adhesive contact between the breathable membrane and the culture plate, a rubber-faced brayer ink-type roller can be used to apply uniform pressure over the surface of the membrane and eliminate any discontinuities or air bubble voids which could lead to such leakage. One such suitable roller is a firm rubber-faced brayer, model #24, lightweight, approximately four inches wide and one inch in diameter, available from the Testrite Instrument Company, Newark, N.J.

I claim:

1. A cell culture plate comprising one or more cells held within a liquid medium contained in a plurality of wells formed and arranged within said plate, wherein said wells are covered and sealed with a waterproof adhesive sealing membrane which excludes microbial contaminants, and is permeable to oxygen and carbon dioxide gases, and wherein a first lower surface of said sealing membrane is coated with a non-cytotoxic pressure-sensitive adhesive material which adheres said sealing membrane to said culture plate.

2. The plate of claim 1, wherein said membrane is sufficiently permeable to said gases to allow cellular respiration to continue.

3. The plate of claim 1, wherein said membrane is designed to allow the transmission rate of said gases through said membrane to be essentially uniform from well to well within said plate.

4. The culture plate of claim 1, wherein said liquid medium is selected from the group consisting of nutrient growth medium, incubation buffer medium, buffered enzyme medium, chemical assay medium, biochemical assay medium, and immunochemical assay medium.

5. The culture plate of claim 1, wherein said sealing membrane comprises a facestock material selected from the group consisting of polyester-polyurethane copolymer film and polyether-polyurethane copolymer film.

6. The culture plate of claim 1, wherein said sealing membrane comprises a facestock selected from the group consisting of polyester-polyurethane copolymer film and polyether-polyurethane copolymer film, wherein said facestock has a thickness ranging between 0.0005 and 0.002 inches.

7. The culture plate of claim 1, wherein said pressure-sensitive adhesive material is a non-cytotoxic pressure-sensitive acrylic adhesive material.

8. A kit comprising a culture plate comprising sample wells formed and arranged within said culture plate, and a sterile sheet assembly comprising a sized portion of the waterproof sealing membrane which excludes microbial contaminants, and is permeable to oxygen and carbon dioxide gases, and which comprises a first lower surface which is coated with a non-cytotoxic pressure-sensitive adhesive material for attaching said membrane to said culture plate.

9. The kit of claim 8, wherein said pressure-sensitive adhesive material is covered and protected by a removable release paper sheet which serves to maintain the sterility of said first lower surface and said pressure-sensitive adhesive material.

10. The kit of claim 8, wherein said pre-sterilized sized portion of membrane comprises a second upper surface which is at least partially covered by a removable upper carrier sheet which aids in the manual handling of said membrane during its alignment and attachment to said culture plate.

11. The kit of claim 10, wherein said removable upper carrier sheet is selected from the group consisting of a peelable transparent plastic sheet, and a peelable release paper frame configured and arranged around the perimeter portion of said membrane.

* * * * *